(12) United States Patent
Inagaki

(10) Patent No.: US 8,459,271 B2
(45) Date of Patent: Jun. 11, 2013

(54) NON-COMBUSTION TYPE FLAVOR SUCTION ARTICLE

(75) Inventor: Michihiro Inagaki, Yokohama (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 13/239,693

(22) Filed: Sep. 22, 2011

(65) Prior Publication Data

US 2012/0006346 A1 Jan. 12, 2012

Related U.S. Application Data

(63) Continuation of application No. PCT/JP2010/054877, filed on Mar. 19, 2010.

(30) Foreign Application Priority Data

Mar. 23, 2009 (JP) ................................. 2009-070534

(51) Int. Cl.
 *A24F 47/00* (2006.01)

(52) U.S. Cl.
 USPC ............ 131/271; 131/329; 131/335; 131/337

(58) Field of Classification Search
 None
 See application file for complete search history.

(56) References Cited

U.S. PATENT DOCUMENTS

| 4,756,318 A | 7/1988 | Clearman et al. |
| 2004/0129280 A1 | 7/2004 | Woodson et al. |
| 2005/0070409 A1 * | 3/2005 | Deal ............................. 493/44 |
| 2007/0235049 A1 * | 10/2007 | Gedevanishvili et al. ..... 131/331 |

FOREIGN PATENT DOCUMENTS

| GB | 2 415 597 A | 1/2006 |
| JP | 5-115272 A | 5/1993 |
| JP | 2003-169851 A | 6/2003 |
| JP | 2006-504431 A | 2/2006 |
| JP | 2008-539717 A | 11/2008 |
| WO | WO 2006/117697 A1 | 11/2006 |
| WO | WO 2006117697 A1 * | 11/2006 |

OTHER PUBLICATIONS

International Search Report for PCT/JP2010/054877, mailed on Jun. 22, 2010.
Japanese Office Action mailed on Oct. 9, 2012 with an English translation.

* cited by examiner

*Primary Examiner* — Michael J Felton
(74) *Attorney, Agent, or Firm* — Birch, Stewart, Kolasch & Birch, LLP

(57) ABSTRACT

A non-combustion type flavor suction article includes a capsule enclosing a liquid flavor in a shell, leak-protection members sandwiching the capsule, a wrapping material made of a flavor-impermeable and heat-conducting material and wrapped around the capsule and the leak-protection members, and a mouthpiece connected to an end of the wrapping material.

10 Claims, 3 Drawing Sheets

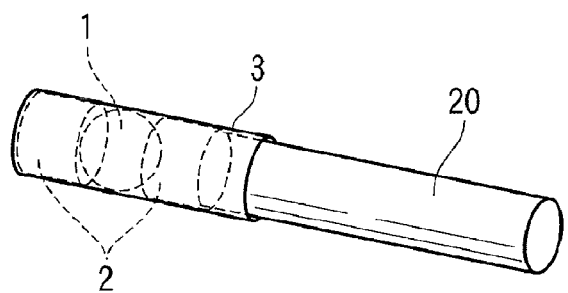
F I G. 1
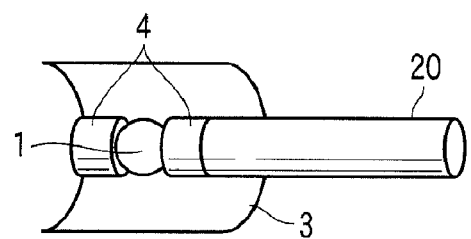
F I G. 2
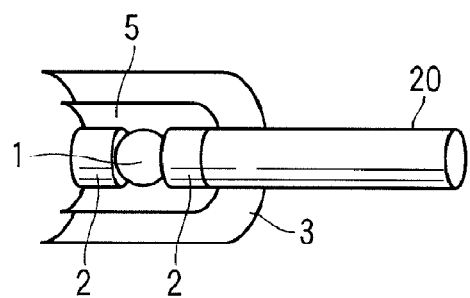
F I G. 3

NON-COMBUSTION TYPE FLAVOR SUCTION ARTICLE

CROSS-REFERENCE TO RELATED APPLICATIONS

This application is a Continuation Application of PCT Application No. PCT/JP2010/054877, filed Mar. 19, 2010 and based upon and claiming the benefit of priority from prior Japanese Patent Application No. 2009-070534, filed Mar. 23, 2009, the entire contents of all of which are incorporated herein by reference.

BACKGROUND OF THE INVENTION

1. Field of the Invention

The present invention relates to a non-combustion type flavor suction article.

2. Description of the Related Art

Conventionally, flavor suction articles include a pipe equipped with a fiber bundle impregnated with a flavor, the pipe being sucked at normal temperature. However, according to the method, the amount of volatilized components is so small that a user cannot be fully satisfied.

On the other hand, when a conventional cigarette is smoked, the smoker ignites an end of a tobacco rod, sucks at an end of the mouthpiece of the cigarette, and inhales air mainly through the ignited end. At that time, the tobacco burns at a temperature higher than 800° C. The burning at such a high temperature may cause various problems, and thus, electric heating cigarettes as alternative cigarettes are developed. In addition, it has been proposed that in an electric heating cigarette, flavor release is controlled by placing flavor-containing beads (Jpn. PCT National Publication No. 2006-504431).

The heating temperature for the electric heating cigarette described in Jpn. PCT National Publication No. 2006-504431 is lower than that in the case of igniting a tobacco. However, the cigarette generates a smoke to be inhaled, and thus still can cause problems of smoke and combustion products.

BRIEF SUMMARY OF THE INVENTION

An object of the present invention is to provide a non-combustion type flavor suction article which allows control of flavor release and the enjoyment of flavor without generation of smoke or combustion products.

A non-combustion type flavor suction article of the present invention comprises: a capsule enclosing a liquid flavor in a shell, leak-protection members sandwiching the capsule, a wrapping material made of a flavor-impermeable and heat-conducting material and wrapped around the capsule and the leak-protection members, and a mouthpiece connected to an end of the wrapping material.

In the present invention, the mouthpiece is preferably made of a flavor-impermeable material. For example, the mouthpiece is made of a paper pipe inner wall of which is coated with a flavor-impermeable material. In the present invention, the shell of the capsule is preferably the one melted by heat. In the present invention, the leak-protection members may be made of a paper filter or acetate filter, or tobacco filler.

In the present invention, the capsule and the leak-protection members may be wrapped with a tobacco sheet in a tubular form, and further wrapped with the wrapping material in a tubular form. The bonding portions of the leak-protection member and the mouthpiece may be wrapped with a tobacco sheet in a tubular form, and the capsule, the leak-protection members, and the tobacco sheet may be further wrapped with the wrapping material in a tubular form.

In the present invention, the number of the capsules sandwiched by the leak-protection members may be one or more. The capsule may be embedded in the leak-protection member.

In the non-combustion type flavor suction article according to the present invention, the shell of the capsule encloses a liquid flavor, so that the flavor is stably retained during storage without volatilization of the flavor. When the article is used, the shell is broken to release the flavor, and the released flavor soaks into the leak-protection members disposed at the both sides of the capsule, and is retained therein without flowing to the mouth of the user. The user sucks the flavor component volatilized by heating, thereby enjoying the flavor.

BRIEF DESCRIPTION OF THE SEVERAL VIEWS OF THE DRAWING

FIG. 1 is a perspective view of the non-combustion type flavor suction article according to one embodiment of the present invention.

FIG. 2 is a partially exploded perspective view of the non-combustion type flavor suction article according to another embodiment of the present invention.

FIG. 3 is a partially exploded perspective view of the non-combustion type flavor suction article according to another embodiment of the present invention.

DETAILED DESCRIPTION OF THE INVENTION

Figure 4:
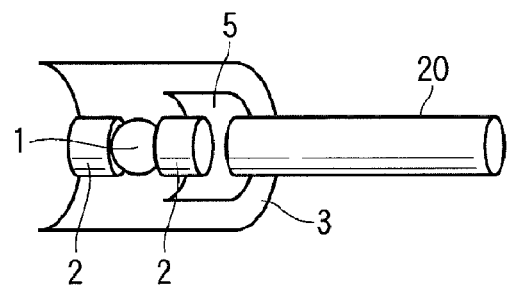
FIG. 4 is a partially exploded perspective view of the non-combustion type flavor suction article according to another embodiment of the present invention.

Hereinafter, the embodiments of the present invention will be described with reference to drawings.

FIG. 1 is a perspective view of the non-combustion type flavor suction article according to one embodiment of the present invention. In FIG. 1, a pair of leak-protection members 2, 2 is arranged so as to sandwich a capsule 1 with a particle size of 4 to 8 mm and encloses a liquid flavor in the shell of the capsule. The leak-protection members 2, 2 are made of, for example, a filter material such as a paper filter or acetate filter. One of the leak-protection members 2 is in contact with an end of a mouthpiece 20 made of a paper pipe inner wall of which is coated with a flavor-impermeable material. A wrapping material 3 made of a flavor-impermeable and heat-conducting material is wrapped around the capsule 1, the leak-protection members 2, 2, and an end of the mouthpiece 20, and thus forming a tube. Hereinafter, the structure composed of the capsule 1 and the leak-protection member 2, 2, wrapped in the wrapping material 3, excluding the mouthpiece 20, is referred to as a roll 10.

In the present invention, the capsule 1 may be made by an ordinary method of capsulation. The shell of the capsule may be made of, for example, gelatin or hydroxypropyl methylcellulose. The shell of the capsule is preferably melted by heat, or may be broken by stress.

In the present invention, the leak-protection member 2 may be made of a filter material such as a paper filter or acetate filter, or tobacco filler.

In the present invention, the wrapping material is made of a flavor-impermeable and heat-conducting material. The wrapping material is preferably made of a metal foil having higher heat conductivity than paper. For example, as the metal foil, the one represented by an aluminum foil or a stainless steel having a heat conductivity of 10 W/m·K or more, cost effectiveness, rust resistance, and high processability (a foil with a thickness of several μm to 10 μm and having high tensile strength and flexibility) is preferably used. The use of a wrapping material made of such a metal foil makes it possible to conduct heat from a heating device, which will be described below, to the capsule uniformly and efficiently.

In the present invention, the mouthpiece 20 is preferably made of a flavor-impermeable material. For example, the mouthpiece 20 is made of a paper pipe inner wall of which is coated with a flavor-impermeable material.

The non-combustion type flavor suction articles according to another embodiment of the present invention will be described below with reference to FIG. 2 to FIG. 6.

The non-combustion type flavor suction article shown in FIG. 2 includes tobacco filler 4 as the leak-protection member.

In the non-combustion type flavor suction article shown in FIG. 3, a tobacco sheet 5 is wrapped around a capsule 1 and leak-protection members 2, 2 to form a tube, and a wrapping material 3 is further wrapped around the tube to form another tube on it.

In the non-combustion type flavor suction article shown in FIG. 4, a tobacco sheet 5 is wrapped around the bonding portions of one of the leak-protection members 2 and a mouthpiece 20 to form a tube, and a wrapping material 3 is further wrapped around a capsule 1, the leak-protection member 2, and a tobacco sheet 4 to form another tube on them.

When the tobacco filler 4 and the tobacco sheet 4 are used as shown in FIGS. 2 to 4, the user can enjoy the flavor from the capsule 1 together with the flavor component generated by heating tobacco.

Figure 5:
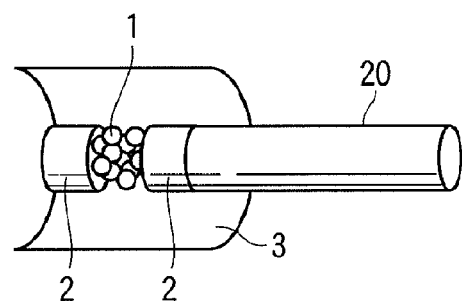
FIG. 5 is a partially exploded perspective view of the non-combustion type flavor suction article according to another embodiment of the present invention.

In the non-combustion type flavor suction article shown in FIG. 5, capsules 1 with a particle size of 0.3 to 4 mm, smaller than the capsule 1 shown in FIG. 1, are sandwiched by leak-protection members 2, 2. In the non-combustion type flavor suction article, as the capsules 1 are gradually melted from the outside with the progress of heat conduction, the flavor persistence, and the stability of flavor generation in puff-by-puff can be expected.

Figure 6:
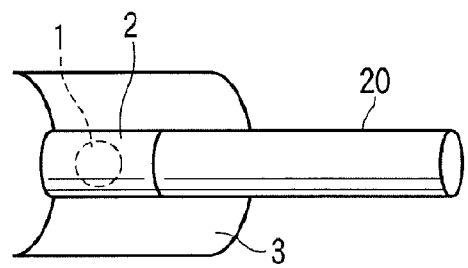
FIG. 6 is a partially exploded perspective view of the non-combustion type flavor suction article according to another embodiment of the present invention.

In the non-combustion type flavor suction article shown in FIG. 6, a capsule 1 is embedded in a leak-protection member 2. In the non-combustion type flavor suction article, the effect of suppressing the exudation of the flavor can be improved.

Next, a heating device used for heating the non-combustion type flavor suction article according to the present invention will be described.

Figure 7:
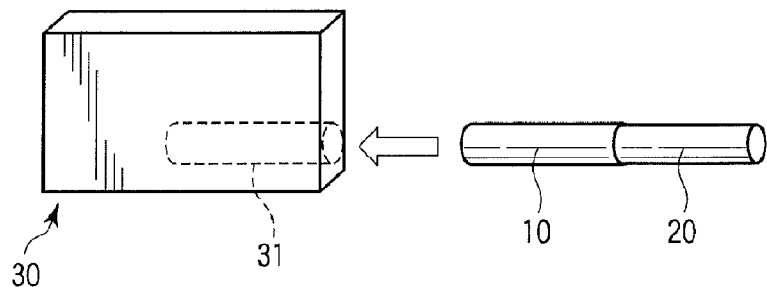
FIG. 7 is an illustration showing the insertion of a non-combustion type flavor suction article into the heater of a heating device.

FIG. 7 is an illustration showing the insertion of a non-combustion type flavor suction article into the heater of the heating device. As shown in FIG. 7, the roll 10 of a non-combustion type flavor suction article is inserted into the heater 31 having a hollow cylindrical structure in the heating device 30. The heater 31 is preferably composed of a hollow cylinder, which is made of the same material as the wrapping material 3 of the roll 10 (for example, aluminum), coated with an electric resistor. If the material of the inner surface of the heater 31 and the material of the wrapping material 3 are different, electrolytic corrosion may undesirably occur.

Figure 8:
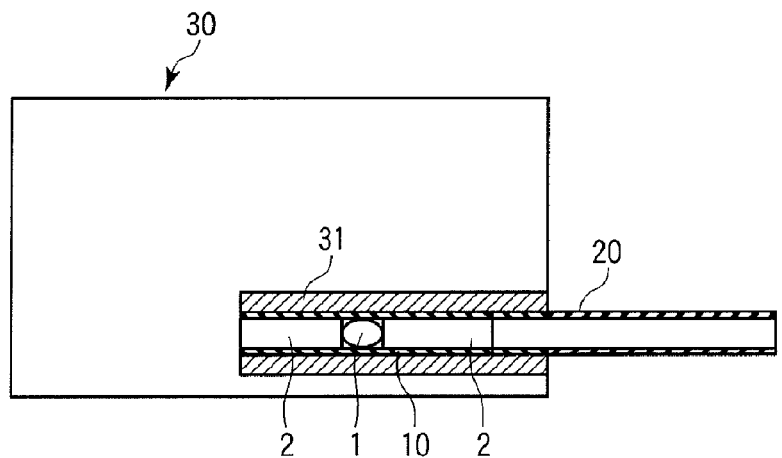
FIG. 8 is a cross-sectional view of a heating device into which a non-combustion type flavor suction article is inserted.

FIG. 8 is a cross-sectional view of a heating device into which a non-combustion type flavor suction article is inserted. The heater 31 having a hollow cylindrical structure in the heating device 30 is heated to a temperature of 80 to 140° C. The roll 10 of a non-combustion type flavor suction article is inserted into the hollow section of the heater 31.

Figure 9:
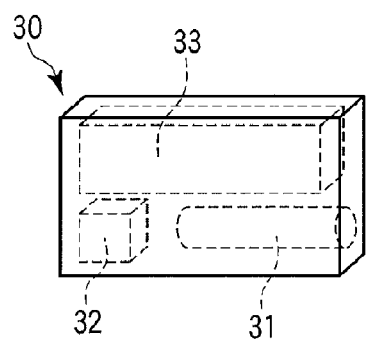
FIG. 9 is a perspective view of a heating device.

FIG. 9 is a perspective view of a heating device 30. As described above, the heating device 30 has the heater 31 having a hollow cylindrical structure. The heating device 30 contains a control circuit 32, a temperature sensor (not shown), and a battery 33.

Examples of the temperature sensor include a thermocouple and a thermistor. The control circuit 32 is powered by the battery 33, and performs feedback control such that the temperature of the heater 31 detected by the temperature sensor ranges from 80 to 140° C.

EXAMPLE

An example of the present invention will be described below. In the present example, the non-combustion type flavor suction article shown in FIG. 1 was produced.

A seamless capsule 1 having a particle size of 6 mm and composed of a gelatin shell enclosing a menthol flavor therein was made. Leak-protection members 2, 2 made of a cylindrical paper filter having a length of 5 mm were arranged at the both sides of the capsule 1, thereby sandwiching the capsule 1. One of the leak-protection members 2 was brought into contact with one end of a mouthpiece 20 made of a paper pipe inner wall of which is coated with a flavor-impermeable material. In that state, a wrapping material 3 made of an aluminum foil was wrapped around the capsule 1, the leak-protection members 2, 2, and one end of the mouthpiece 20 to form a tube, and thus making a non-combustion type flavor suction article.

As shown in FIG. 7, the non-combustion type flavor suction article was inserted into a heating device 30, and a portion corresponding to the capsule 1 was heated to 115° C. As a result, the shell of the capsule 1 was melted in several seconds, and it was confirmed that the flavor soaked into the leak-protection member 2 made of a paper filter. Good feeling of the menthol flavor was enjoyed by suction through the mouthpiece 20 without leakage of the liquid to the outside.

What is claimed is:

1. A non-combustion type flavor suction article comprising:
    a capsule enclosing a liquid flavor in a shell;
    leak-protection members sandwiching the capsule;
    a wrapping material made of a flavor-impermeable and heat-conducting material and wrapped around the capsule and the leak-protection members;
    a mouthpiece connected to an end of the wrapping material; and
    a heating device comprising a heater having a hollow cylindrical structure, into which are inserted the wrapping material that is wrapped around the capsule and the leak-protection members.

2. The non-combustion type flavor suction article of claim 1, wherein the mouthpiece is made of a flavor-impermeable material.

3. The non-combustion type flavor suction article of claim 1, wherein the mouthpiece is made of a paper pipe, an inner wall of which is coated with a flavor-impermeable material.

4. The non-combustion type flavor suction article of claim 1, wherein the shell of the capsule is melted by heat.

5. The non-combustion type flavor suction article of claim 1, wherein the leak-protection members are made of a paper filter or an acetate filter.

6. The non-combustion type flavor suction article of claim 1, wherein the leak-protection members are made of tobacco filler.

7. The non-combustion type flavor suction article of claim 1, wherein the capsule and the leak-protection members are wrapped with a tobacco sheet in a tubular form, and further wrapped with the wrapping material in a tubular form.

8. The non-combustion type flavor suction article of claim 1, wherein bonding portions of the leak-protection member and the mouthpiece is wrapped with a tobacco sheet in a tubular form, and the capsule, the leak-protection members, and the tobacco sheet are further wrapped with the wrapping material in a tubular form.

9. The non-combustion type flavor suction article of claim 1, wherein a plurality of capsules is sandwiched by the leak-protection members.

10. The non-combustion type flavor suction article of claim 1, wherein the capsule is embedded in the leak-protection member.

* * * * *